United States Patent [19]

Hess

[11] 4,094,899
[45] June 13, 1978

[54] OXAPROSTAGLANDINS

[75] Inventor: Hans-Jurgen E. Hess, Old Lime, China /Taiwan

[73] Assignee: Pfizer Inc., New York, N.Y.

[21] Appl. No.: 355,644

[22] Filed: Apr. 30, 1973

Related U.S. Application Data

[63] Continuation-in-part of Ser. No. 259,215, Jun. 2, 1972, abandoned.

[51] Int. Cl.$^2$ .................................. C07C 177/00
[52] U.S. Cl. .................. 260/514 D; 260/345.9 P; 260/343.3 P; 260/946; 260/345.7 P; 424/317; 542/426; 560/106; 560/231
[58] Field of Search ............................ 260/468, 514 D

[56] References Cited

U.S. PATENT DOCUMENTS 3,843,713  10/1974  Finch et al. ........................ 260/468

FOREIGN PATENT DOCUMENTS 7,209,738  1/1973  Netherlands .................. 260/468

*Primary Examiner*—Robert Gerstl
*Attorney, Agent, or Firm*—Connolly and Hutz

[57] ABSTRACT

ω-trisnorprostaglandins having at the 17-position two hydrogen atoms and one substituent of the formula:

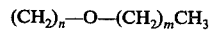

wherein n is an integer of from 0 to 1, m is an integer of from 0 to 4; and having at the 15-position one hydrogen substituent or alkyl substituent of from 1 to 3 carbon atoms. The novel prostaglandins of this invention have been found to have activity profiles comparable to the parent prostaglandins, but exhibit a greater tissue specificity of action.

4 Claims, No Drawings

OXAPROSTAGLANDINS

CROSS-REFERENCE TO RELATED APPLICATION

This application is a continuation-in-part of application Ser. No. 259,215 filed June 2, 1972 and now abandoned.

BACKGROUND OF THE INVENTION

This invention relates to certain novel analogs of the naturally occurring prostaglandins. In particular, it relates to novel 18-oxa, 19-oxa, and 19-oxa-ω-homo-prostaglandins and various novel intermediates and reagents useful in their preparation.

The prostaglandins are C-20 unsaturated fatty acids which exhibit diverse physiological effects. For instance, the prostaglandins of the E and A series are potent vasodilators (Bergstrom, et al., Acta Physiol. Scand. 64:332-33, 1965 and Bergstrom, et al., Life Sci. 6:449-455, 1967) and lower systemic arterial blood pressure (vasodepression) on intravenous administration (Weeks and King, Federation Proc. 23:327, 1964; Bergstrom, et al., 1965, op. cit.; Carlson, et al., Acta. Med. Scand. 183:423-430, 1968; and Carlson, et al., Acta Physiol. Scand. 75:161-169, 1969). Another well known physiological action for $PGE_1$ and $PGE_2$ is as a bronchodilator (Cuthbert, Brit. Med. J. 4:723-726, 1969).

Still another important physiological role for the natural prostaglandins is in connection with the reproductive cycle. $PGE_2$ is known to possess the ability to induce labor (Karim, et al., J. Obstet Gynaec. Brit. Cwlth. 77:200-210, 1970), to induce therapeutic abortion (Bygdeman, et al., Contraception, 4, 293 (1971) and to be useful for control of fertility (Karim, Contraception, 3, 173 (1971)). Patents have been obtained for several prostaglandins of the E and F series as inducers of labor in mammals (Belgian Pat. No. 754,158 and West German Pat. No. 2,034,641), and on $PGF_1$, $F_2$, and $F_3$ for control of the reproductive cycle (South African Pat. No. 69/6089).

Still other known physiological activities for $PGE_1$ are in the inhibition of gastric acid secretion (Shaw and Ramwell, In: Worcester Symp. on Prostaglandins, New York, Wiley, 1968, p. 55-64) and also of platelet aggregation (Emmons, et al., Brit. Med. J. 2:468-472, 1967).

It is now known that such physiological effects will be produced in vivo for only a short period, following the administration of a prostaglandin. A substantial body of evidence indicates that the reason for this rapid cessation of activity is that the natural prostaglandins are quickly and efficiently metabolically deactivated by β-oxidation of the carboxylic acid side-chain and by oxidation of the 15α-hydroxyl group (Anggard, et al., Acta. Physiol. Scand., 81, 396 (1971) and references cited therein).

It was, of course, considered desirable to create analogs of the prostaglandins which would have physiological activities equivalent to the natural compounds, but in which the selectivity of action and the duration of the activity would be increased. Increased selectivity of action would be expected to alleviate the severe side effects, particularly gastrointestinal side effects, frequently observed following systemic administration of the natural prostaglandins (see Lancet, 536, 1971).

SUMMARY OF THE INVENTION

The novel compounds of the present invention, the ω-trisnorprostaglandins having at the 17-position two hydrogen atoms and one substituent of the formula:

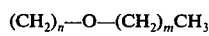

wherein n is an integer of from 0 to 1, m is an integer of from 0 to 4; and having at the 15-position one hydrogen substituent or one alkyl substituent of from 1 to 3 carbon atoms, uniquely satisfy the above mentioned requirements. That is, they possess activity profiles comparable to the parent prostaglandins, although they are more tissue selective in their action and they exhibit a longer duration of action than the parent prostaglandins.

Especially preferred are ω-trisnorprostaglandins of the A, E, or F series having at the 17-position two hydrogen atoms and one substituent of the formula:

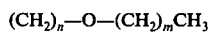

wherein n is an integer of from 0 to 1, m is an integer of from 0 to 4; and having at the 15-position one hydrogen substituent or one alkyl substituent of from 1 to 3 carbon atoms.

The present invention comprises novel prostaglandins, novel intermediates, and novel reagents of the formulae:

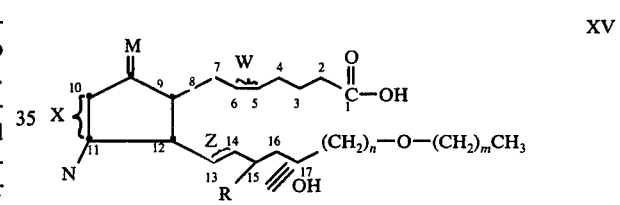

XV

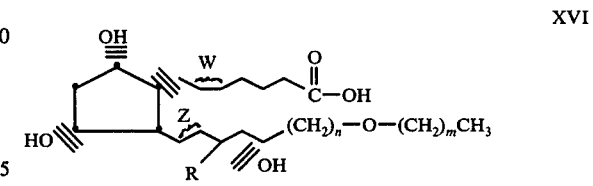

XVI

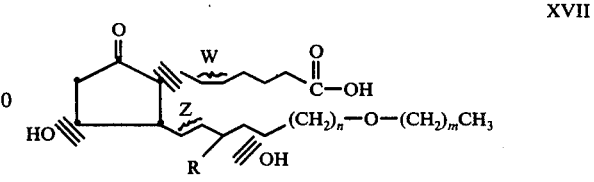

XVII

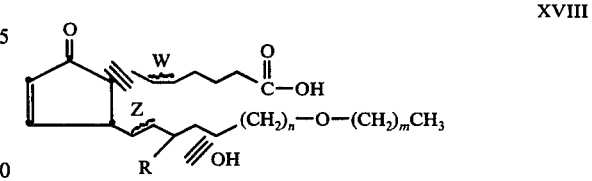

XVIII

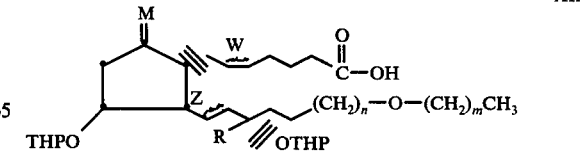

XIX

3

-continued

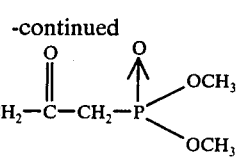

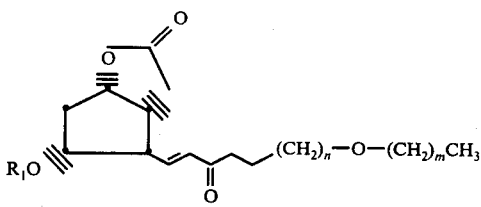
III

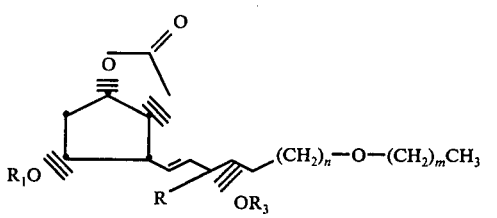
V

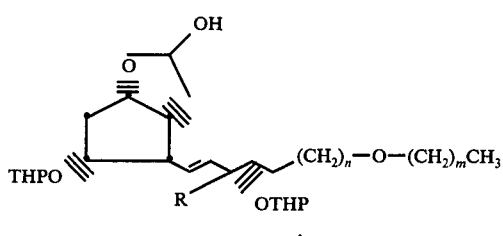
and

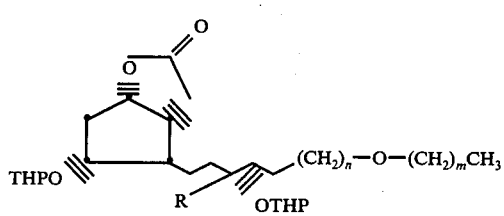
XII

4 wherein:
R is hydrogen or alkyl of from 1 to 3 carbon atoms;
$R_1$ is hydrogen, 2-tetrahydropyranyl, or

wherein $R_2$ is alkyl of from 1 to 5 carbon atoms, phenyl, or p-biphenyl;
$R_3$ is hydrogen or 2-tetrahydropyranyl;
n is an integer of from 0 to 1;
m is an integer of from 0 to 4
W and X are each single bond or a cis double bond;
Z is a single bond or a trans double bond;
M is keto,

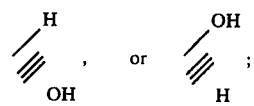

N is hydrogen or α-hydroxyl; and
THP is 2-tetrahydropyranyl.
Especially preferred novel prostaglandins of this invention are:
9-oxo-11α,15α-dihydroxy-19-oxa-cis-5-trans-13-prostadienoic acid;
9-oxo-11α,15α-dihydroxy-19-oxa-cis-5-trans-13-ω-homoprostadienoic acid;
9-oxo-11α,15α-dihydroxy-18-oxa-cis-5-trans-13-prostadienoic acid;
9α,11α,15α-trihydroxy-19-oxa-cis-5-trans-13-prostadienoic acid;
9α,11α,15α-trihydroxy-19-oxa-cis-5-trans-13-ω-homoprostadienoic acid;
9α,11α,15α-trihydroxy-18-oxa-cis-5-trans-13-prostadienoic acid.
Other novel and useful oxaprostaglandin analogs are the $C_9$, $C_{11}$, and $C_{15}$ esters wherein said esterifying group is formyl, alkanoyl having from 2 to 5 carbon atoms, or benzoyl.

REACTION SCHEME A

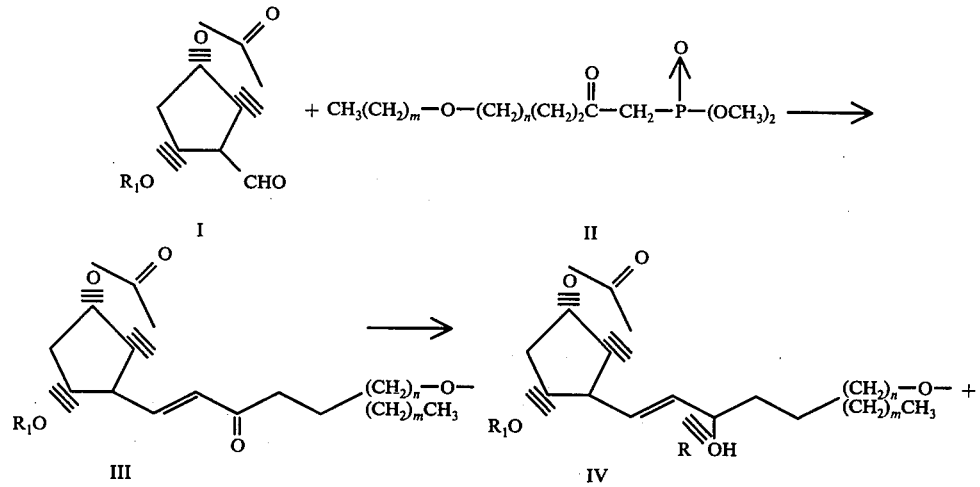

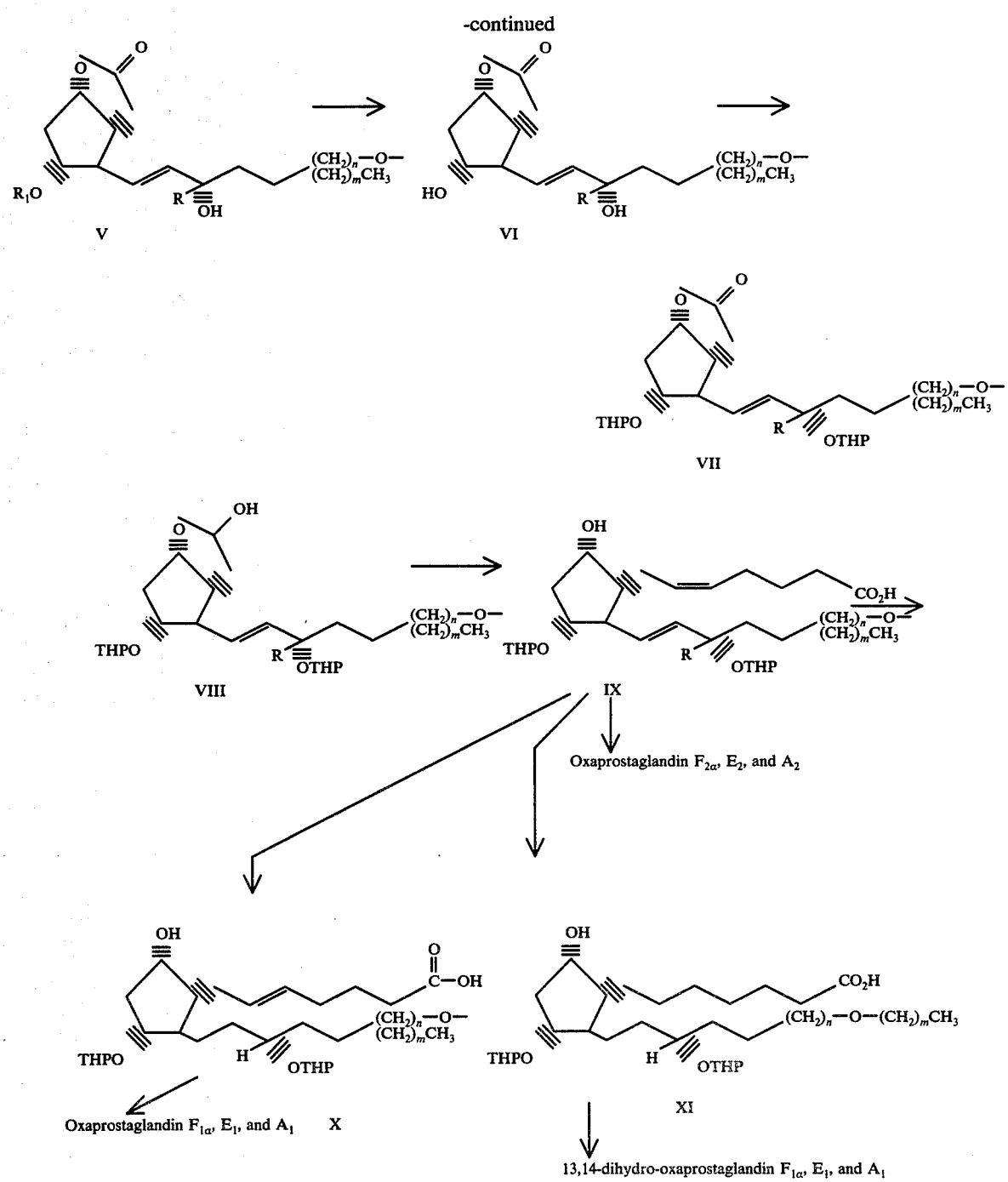
REACTION SCHEME B
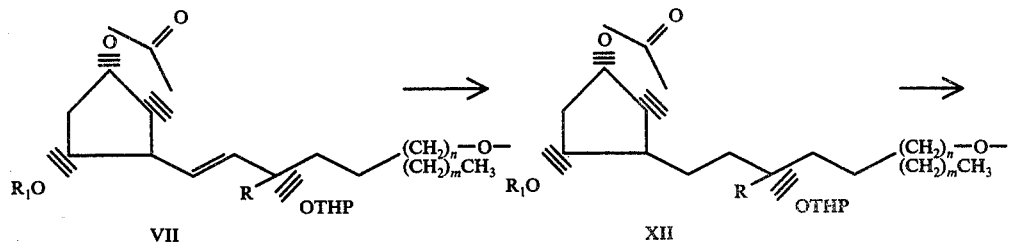

-continued
REACTION SCHEME B

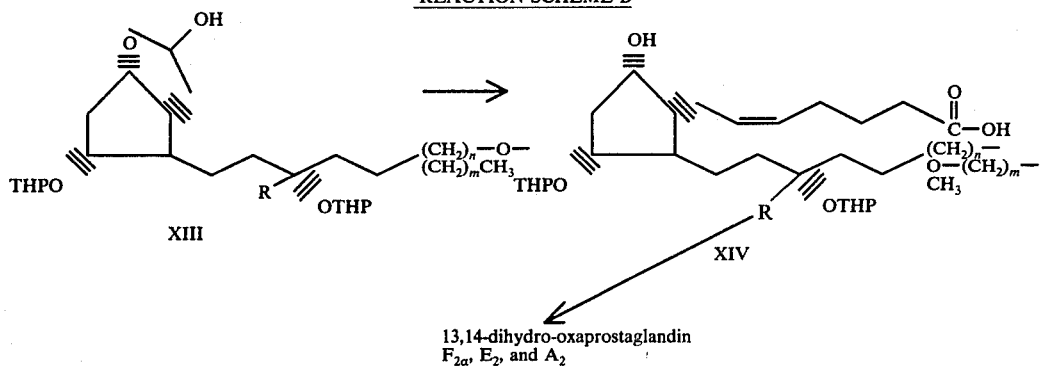

13,14-dihydro-oxaprostaglandin
$F_{2\alpha}$, $E_2$, and $A_2$

As shown in Reaction Scheme A, Aldehyde I is caused to react with the novel reagent II to produce ketone III. The reactants are employed in substantially equimolar proportions and the reaction is preferably run for about 30 minutes.

III is treated with 1,2-dimethoxyethane and zinc borohydride, for about 1 hour, to produce alcohols IV and V which are then separated using, for example, column chromatography with ether as eluent. If the 15-lower akyl derivative is desired, lower alkyl lithium, such as methyl lithium, is added to III at this time.

V-VI involves treatment with anhydrous potassium carbonate for about 1 hour, followed by hydrochloric acid and extraction, for example, with ethyl acetate and finally concentration.

VI-VII requires treatment with 2,3-dihydropyran and p-toluene-sulfonic acid for about 15 minutes in a nitrogen atmosphere, and then combination with ether, washing with, for example, sodium bicarbonate and then brine, and then concentration.

VII-VIII is performed by reaction for about 1 hour with diisobutylaluminum hydride in n-hexane cooled to $-78°$ C. in a nitrogen atmosphere. The mixture is then mixed with ether, washed, dried, and concentrated.

VIII-IX is brought about by reaction with (4-carbohydroxy-n-butyl)-triphenylphosphonium bromide and methylsulfinylmethide in dimethyl sulfoxide at room temperature for at least 2 hours. The mixture is then acidified with, for example, aqueous hydrochloric acid, and then is extracted with ethyl acetate, evaporated, and concentrated.

IX—Oxaprostaglandin $F_{2\alpha}$ involves hydrolysis with aqueous acetic acid, concentration, and purification by column chromatography.

IX—Oxaprostaglandin $E_2$ requires treatment with Jones reagent for about 20 minutes at $-10°$ C. to form a second intermediate before the acid treatment and purification as above.

Oxaprostaglandin $A_2$ is obtained by treating oxaprostaglandin $E_2$ with formic acid, concentration, and purification by column chromatography.

IX—Oxaprostaglandin $F_{1\alpha}$ requires a reduction with palladium on carbon and methanol to produce X which may then be hydrolysed with aqueous acetic acid, and purified as above.

X—Oxaprostaglandin $E_1$—Oxaprostaglandin $A_1$ follows exactly the same method as outlined for the $PGE_2$-$PGA_2$ series above.

IX—13,14-dihydro-oxaprostaglandin $F_{1\alpha}$ requires a reduction with palladium on carbon and methanol to produce XI which is then hydrolysed with aqueous acetic acid, and purified as above. To produce the other 13,14-dihydro derivatives one follows the procedures outlined above.

Referring now to Reaction Scheme B, Lactone VII is reduced with palladium on carbon to form XII, which is then treated with diisobutyl aluminum hydride to produce Hemiacetal XIII.

XIII-XIV is analogous to VIII-IX of Reaction Scheme A.

XIV—13,14-dihydro-oxaprostaglandin $F_{2\alpha}$ involves hydrolysis with aqueous acetic acid, concentration, and purification by column chromatography.

XIV—13,14-dihydro-oxaprostaglandin $E_2$ requires treatment with Jones reagent for about 20 minutes at $-10°$ C. to form a second intermediate before acid treatment and purification as above.

13,14-dihydro-oxaprostaglandin $A_2$ is obtained by treating 13,14-dihydro-oxaprostaglandin $E_2$ with formic acid, concentrating, and purifying by column chromatography.

Novel reagent II is prepared by contacting an appropriate phosphonate, such as dimethyl methyl phosphonate, in reaction inert solvent such as tetrahydrofuran and in a nitrogen atmosphere, with an organo-lithium compound, such as n-butyllithium. Then an appropriate alkoxy ester, such as methyl 4-methoxybutyrate is added, and the product is purified by extraction in methylene chloride and it is concentrated.

The novel alkanoates, formates, and benzoates of the E, F and A series of oxaprostaglandins are prepared by reaction of the appropriate prostaglandins with an acid chloride. For example, 19-oxa $PGE_2$ when reacted with benzoyl chloride, in the presence of a tertiary amine in a reaction-inert solvent, will yield 11,15-dibenzoyl-19-oxa $PGE_2$ and, in the same way, 18-oxa $PGF_{2\alpha}$ when reacted with pivaloyl chloride will yield 9,11,15-tripivaloyl-18-oxa $PGF_{2\alpha}$.

As the literature cited under "Background of the Invention" establishes, the natural prostaglandins are known to exhibit a spectrum of physiological activities. In numerous in vivo and in vitro tests we have demonstrated that the exaprostaglandin analogs have the same physiological activities as exhibited by the natural prostaglandins. These tests include, among others, a test for effect on isolated smooth muscle from guinea pig ileum and rat uterus, a test for effect on histamine induced bronchospasm in guinea pig, a test for effects on dog blood pressure, a test for induction of diarrhea in mice, and a test for the induction of abortion in early pregnant rats.

Results on these various physiological tests are shown in Table I below. It will be noted that not only do these oxaprostaglandin analogs possess comparable action quantitatively to the natural prostaglandin, but they also possess the advantage of tissue selectivity, particularly 19-oxaprostaglandin $E_2$. On the basis of the difference seen in the rat uterus and guinea pig ileum tests with 19-oxaprostaglandin $E_2$, one would expect to have a reduction of the unpleasant gastrointestinal side effects which were encountered when natural $PGE_2$ was employed as an abortion inducer (Lancet, 536, 1971). This important advantage has been amply verified by the fact that 19-oxaprostaglandin $E_2$ has now been found to be only 10% as effective as natural $PGE_2$ in inducing diarrhea in mice in vivo, while it is as effective as natural $PGE_2$ in inducing abortion in the early pregnant rat. Furthermore, as can be seen from Table I, 18-oxa $PGE_2$ is particularly selective with regard to its blood pressure effects, while 19-oxa-$\omega$-homo $PGE_2$ is a more selective bronchodilator than natural $PGE_2$.

TABLE I

| Prostaglandin | Dog Blood Pressure[a] | Histamine Aerosol[b] | Rat Uterus[c] ng/ml | Guinea pig Ileum[d] ng/ml | K[e] |
|---|---|---|---|---|---|
| 19-oxa $PGE_2$ | 20 | 19% | 50–100 | 100–500 | $2.5 \times 10^{-6}$M |
| 19-oxa-$\omega$-homo-$PGE_2$ | 4 | 38% | 100 | 100 | $4 \times 10^{-6}$M |
| 18-oxa $PGE_2$ | 2 | 3% | 100–300 | 100–300 | — |
| 19-oxa $PGF_{2\alpha}$ | — | — | 100–500 | 100–500 | — |
| 19-oxa-$\omega$-homo-$PGF_{2\alpha}$ | — | — | 60–300 | $\geq$100 | — |
| 18-oxa $PGF_{2\alpha}$ | — | — | 300–600 | 100–300 | — |
| $PGE_2$ | 1 | 75% | 10–30 | 10–30 | $4 \times 10^{-7}$M |

[a] Relative dose at which oxaprostaglandin derivative has similar action to $PGE_2$ for depressor effect on anesthetized dog blood pressure.
[b] Per cent protection by 100 $\mu$g/ml aerosol dose for histamine induced bronchospasm in the guinea pig.
[c] Threshold dose for spasmogenic effect on estrogenized rat uterus in vitro.
[d] Threshold dose for spasmogenic effect on guinea pig ileum in vitro.
[e] Inhibition constant for norepinephrine stimulated lipolysis.

The physiological responses observed in these tests are useful in determining the utility of the test substance for the treatment of various natural and pathological conditions. Such determined utilities include: antihypertensive activity, bronchodilator activity, antithrombogenic activity, antiulcer activity, smooth muscle activity [useful as anti-fertility agent, for the induction of labor, and as an abortifacient], and anti-fertility activity through a mechanism not affecting smooth muscle, for example, luteolytic mechanisms.

The novel compounds of this invention possess more selective activity profiles than the corresponding naturally occurring prostaglandins and, in many cases, exhibit a longer duration of action. For example, if an intravaginal treatment for abortion induction is desired, a suitable vehicle is a tampon impregnated with 19-oxa-$\omega$-homoprostaglandin $F_{2\alpha}$ or lactose tablets of the same agent. In such treatments a suitable dose would be about 100 mg. with 1 or 2 doses being employed.

In cases where a midterm abortion is necessary, an effective agent would be physiological NaCl solution of 19-oxa-$PGE_2$ administered as an intravenous infusion. A suitable dosage could be from about 5 to 100 $\mu$g/min administered for a period of from about 2 to 10 hours.

Another use for the oxaprostaglandins of the F-series is as an inducer of labor. For this purpose a physiological NaCl solution of an oxa-PGF is employed as an intravenous infusion in the amount of from about 5 to 100 $\mu$g/kg/min for from about 1 to 10 hours, or is administered orally at doses of 5 to 100 mg. every 2 hours.

Still other applications for the oxaprostaglandins are to produce bronchodilation or to increase nasal patency. An appropriate dosage form for this use is an ethanolic solution of 19-oxa-$\omega$-homo-$PGE_2$ employed as an aerosol using fluorinated hydrocarbons as propellant in the amount of from about 50–500 $\mu$g/dose.

Oxaprostaglandins of the A series are useful hypotensive agents, as are those of the E series. For treatment of hypertension these compounds are administered as intravenous injections at doses of about 0.5–10 $\mu$g/kg or preferably orally in the form of capsules or tablets at doses of 0.005 to 0.5 mg/kg/day.

The novel 15-lower alkyl compounds of this invention have the same profile of activity as the prostaglandin analogs of this invention, where R is hydrogen, from which they are derived. Their special utility is concerned with the fact that their duration of action is much increased over the above said compounds, where R is hydrogen, and in such cases where this is essential the 15-lower alkyl compounds are usually preferred. The prostaglandin analogs which have a beta hydroxyl at $C_{15}$ and possess a $C_{15}$ lower alkyl group have action which is similar to their epimers. In some cases, however, the selectivity that these compounds display exceeds that of the epimeric compounds. Furthermore, the prostaglandins of the $PGF_\beta$ series have substantially the same activities as prostaglandins of the $PGF_\alpha$ series as do the $C_9$, $C_{11}$, and $C_{15}$ esters of all the novel prostaglandins of this invention. The latter are especially appropriate for oral dosage preparations.

The new compounds of this invention can be used in a variety of pharmaceutical preparations which contain the compound or a pharmaceutically acceptable salt thereof, and they may be administered in the same manner as natural prostaglandins by a variety of routes, such as intravenous, oral and topical, including aerosol, intravaginal, and intranasal, among others. Pharmaceutically acceptable salts include salts of pharmaceutically acceptable bases such as alkali and alkaline earth metals, ammonia, and amines.

To prepare any of the above dosage forms or any of the numerous other forms possible, various reaction-inert diluents, excipients or carriers may be employed. Such substances include, for example, water, ethanol, gelatins, lactose, starches, magnesium stearate, talc, vegetable oils, benzyl alcohols, gums, polyalkylene glycols, petroleum jelly, cholesterol, and other known carriers for medicaments. If desired, these pharmaceutical compositions may contain auxiliary substances such as preserving agents, wetting agents, stabilizing agents, or other therapeutic agents such as antibiotics.

The following examples are merely illustrative, and in no way limit the scope of the appended claims.

EXAMPLE I

A solution of 12.4 g. (100 mmoles) dimethyl methylphosphonate (Aldrich) in 125 ml. dry tetrahydrofuran was cooled to −78° in a dry nitrogen atmosphere. To the stirred phosphonate solution was added 45 ml. of 2.37 M n-butyllithium in hexane solution dropwise over a period of 30 minutes at such a rate that the reaction temperature never rose above −65°. After an additional 5 minutes stirring at −78°, 6.6 g. (50.0 mmole) methyl 4-methoxybutyrate [prepared by the method of R. Huisgen and J. Reinertshafter, Am., 575, 197 (1952)] was added dropwise at a rate that kept the reaction temperature less than −70° (10 minutes). After 3 hours at −78° the reaction mixture was allowed to warm to ambient temperature, neutralized with 6 ml. acetic acid and rotary evaporated to a white gel. The gelatinous material was taken up in 25 ml. water, the aqueous phase extracted with 100 ml. portions of methylene chloride (3x), the combined organic extracts dried (MgSO$_4$), and concentrated (water aspirator) to a crude residue and distilled, b.p. 141°–145° (1.7–0.6 mm) to give 7.6 g. (68%) dimethyl 2-oxo-6-oxahepthylphosphonate.

Vapor phase chromatography analysis (a 5 foot × ¼ inches column containing 10% SE 30 on Chromosorb P, 80–100 mesh at 105° was employed) indicated a purity ≧ 99.9%. The nmr spectrum (CDCl$_3$) showed a doublet centered at 3.78 δ (J = 11.5 cps, 6H) for

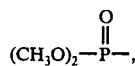

a triplet centered at 3.37 δ (2H) for CH$_3$—O—CH$_2$—CH$_2$—, a singlet at 3.28 δ (3H) for CH$_3$—O—CH$_2$—, a doublet centered at 3.14 δ (J = 23 cps, 2H)

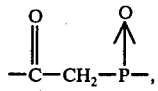

a triplet centered at 2.71 δ (2H) for

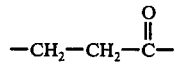

and a multiplet 1.57–2.10 δ (2H) for —CH$_2$—CH$_2$—CH$_2$.

EXAMPLE II

Dimethyl 2-oxo-6-oxaheptylphosphonate as prepared in Example I (1.68 g., 7.5 mmole), in 125 ml. anhydrous ether was treated with 2.5 ml. (5.9 mmole) 2.37M n-butyllithium in n-hexane in a dry nitrogen atmosphere at room temperature. After 5 minutes of stirring, an additional 225 ml. of anhydrous ether wad added followed by 1.75 g. (5.0 mmole) 2-[3α-p-phenylbenzoyloxy-5α-hydroxy-2β-formylcyclopentan-1α-yl]acetic acid, γ-lactone in one portion. After 30 minutes the reaction mixture was quenched with 2.5 ml. glacial acetic acid, diluted with 200 ml. anhydrous ether, washed with 200 ml. 10% HCl (2 x), 200 ml. saturated sodium bicarbonate solution (1 x), 100 ml. water (1 x), dried (MgSO$_4$) and evaporated to yield 1.972 g. (88%) 2-[3α-p-phenylbenzoyloxy-5α-hydroxy-2β-(3-oxo-7-oxa-trans-1octen-1-yl)cyclopenta-1α-yl]acetic acid, γ-lactone as an oil.

The ir spectrum (CHCl$_3$) of the product exhibited adsorption bands at 1770 cm$^{-1}$ (strong), 1717 cm$^{-1}$ (strong), 1675 cm$^{-1}$ (medium) and 1630 cm$^{-1}$ (medium) attributable to the carbonyl groups. The uv spectrum had a λ$_{max}$ = 274 mμ and ε$_{max}$ = 21,380 (ethanol solution). The nmr spectrum (CDCl$_3$) exhibited a multiplet at 7.23–8.18 δ (9H) for the p-biphenyl group, a doublet of doublets centered at 6.71 δ (1H, J = 7.16 cps) and a doublet centered at 6.27 δ (1H, J = 16 cps) for the olefinic protons, a triplet at 3.30 δ (2H) for CH$_2$—CH$_2$—O—CH$_3$, a singlet at 3.21 δ (3H) for —CH$_2$—O—CH$_3$, and multiplets at 4.90–5.50 δ (2H), 2.21–3.07 δ (8H) and 1.58–2.06 δ (2H) for the remainder of the protons.

EXAMPLE III

To a solution of 1972 mg. (4.4 mmole) 2-[3α-p-phenylbenzoyloxy5α-hydroxy-2β-(3-oxo-7-oxa-trans-1-octen-1-yl)cyclopent-1α-yl]acetic acid, γ-lactone as prepared in Example II in 15 ml. dry 1,2-dimethoxyethane in a dry nitrogen atmosphere at ambient temperature was added dropwise 4.0 ml. of a 0.5 M zinc borohydride solution. After stirring at room temperature for 1 hour, the reaction mixture was cooled to 0° and a saturated sodium bitartrate solution was added dropwise until hydrogen evolution ceased. The reaction mixture was allowed to stir for 5 minutes at which time 250 ml. dry methylene chloride was added. After dryin (MgSO$_4$) and concentrating (water aspirator) the resultant semisolid was purified by column chromatography on silica gel (Baker "Analyzed" Reagent 60–200 mesh) using ether as eluent. After elution of less polar impurities, fractions containing 450 mg. 2-[3α-p-phenylbenzoyloxy-5α-hydroxy-2β-(3α-hydroxy-7-oxa-trans1-octen-1-yl)cyclopent-1α-yl]acetic acid, γ-lactone, 294 mg. of 2-[3α-p-phenylbenzoyloxy-5α-hydroxy-2β-(3β-hydroxy-7-oxa-trans-1-octen-1-yl) cyclopent-1α-yl]acetic acid, γ-lactone, and 486 mg. of the two mixed were eluted.

The ir spectrum (CHCl$_3$) of the first of these two compounds had strong carbonyl adsorptions at 1770 and 1715 cm$^{-1}$.

EXAMPLE IV

A heterogeneous mixture of 450 mg. (1.0 mmole) of 2-[3α-p-phenylbenzoyloxy-5α-hydroxy-2β-(3α-hydroxy-7-oxa-trans-1-octen-1-yl)cyclopent-1α-yl]acetic acid, γ-lactone as prepared in Example III, 4.5 ml. of absolute methanol and 140 mg. of finely powdered, anhydrous potassium carbonate was stirred at room temperature for one hour, then cooled to 0°. To the cooled solution was added 2.0 ml. (2.0 mmole) of 1.0N aqueous hydrochloric acid. After stirring at 0° for an additional 10 minutes, 5 ml. of water was added with concomitant formation of methyl p-phenylbenzoate which was collected by filtration. The filtrate was saturated with solid sodium chloride, extracted with ethyl acetate (4 × 10 ml.), the combined organic extracts were washed with saturated sodium bicarbonate (10 ml.), dried (MgSO$_4$) and concentrated to give 204 mg. (76%) of viscous, oily 2-[3α,5α-dihydroxy-2β-(3α-hydroxy-7-oxa-trans-1-octen-1-yl)cyclopent-1α-yl]acetic acid, γ-lactone.

The ir spectrum (CHCl$_3$) exhibited a strong adsorption at 1770 cm$^{-1}$ for the lactone carbonyl and medium adsorption at 960 cm$^{-1}$ for the trans-double bond.

EXAMPLE V

To a solution of 192 mg. (0.71 mmole) 2-[3α,5α-dihydroxy-2β-(3α-hydroxy-7-oxa-trans-1-octen-yl)cyclopent-1α-yl]acetic acid, γ-lactone as prepared in Example IV, in 5 ml. anhydrous methylene chloride and 1 ml. of 2,3-dihydropyran at 0° in a dry nitrogen atmosphere was added 5 mg. p-toluenesulfonic acid, monohydrate. After stirring for 15 minutes, the reaction mixture was combined with 100 ml. ether, the ether solution washed with saturated sodium bicarbonate (1 × 15 ml.) then saturated brine (1 × 15 ml.), dried (MgSO$_4$) and concentrated to yield 310 mg. (100%) 2-[5α-hydroxy-3α-(tetrahydropyrahn-2-yloxy)-2β-(3α-[tetrahydropyran-2-yloxy]-7-oxa-trans-1-octen-1-yl)cyclopent-1α-yl]acetic acid, γ-lactone.

The nmr spectrum (CDCl$_3$) exhibited a multiplet at 5.30–5.62 δ (2H) for the olefinic protons, a singlet at 3.34 δ (3H) for the methyl ether protons, and multiplets at 4.36–5.18 δ (4H), 3.22–4.24 δ (9H), and 1.18–2.92 δ (2OH) for the remaining protons.

EXAMPLE VI

A solution of 310 mg. (0.71 mmole) 2-[5α-hydroxy-3α-(tetrahydropyran-2-yloxy)-2β-3α-[tetrahydropyran-2-yloxy]-7-oxa-trans-1-octen-1-yl)cyclopent-1α-yl, acetic acid, γ-lactone as prepared in Example V in 5 ml. dry toluene was cooled to −78° in a dry nitrogen atmosphere. To this cooled solution was added 1.5 ml. of 20% diisobutylaluminum hydride in n-hexane dropwise at such a rate that the internal temperature never rose about −65° (15 minutes). After an additional 45 minutes of stirring at −78°, anhydrous methanol was added until gas evolution ceased and the reaction mixture was allowed to warm to room temperature. The reaction mixture was combined with 100 ml. ether, washed with 50% sodium potassium tartrate solution (4 × 20 ml.), dried (MgSO$_4$) and concentrated to yield 290 mg. (93%) 2-[5α-hydroxy-3α-(tetrahydropyran-2-yloxy)-2β-(3α-[tetrahydropyran-2-yoxy]-7-oxa-trans-1-octen-1-yl)cyclopent-1-yl]acetaldehyde, γ-hemiacetal.

EXAMPLE VII

To a solution of 870 mg. (2.0 mmole) (4-carbohydroxy-n-butyl) triphenylphosphonium bromide in a dry nitrogen atmosphere in 5.0 ml. dry dimethyl sulfoxide was added 2.0 ml. (4.4 mmole) of a 2.2M solution of sodium methylsulfinylmethide in dimethyl sulfoxide. To this red ylide solution was added dropwise a solution of 290 mg. (0.66 mmole) 2-[5α-hydroxy-3α-(tetrahydropyran-2-yloxy)-2β-(3α-[tetrahydropyran-2-yloxy]-7-oxa-trans-1-octen-1-yl)cyclopent-1α-yl]acetaldehyde, γ-hemiacetal as prepared in Example VI in 3.0 ml. dry dimethyl sulfoxide over a period of 20 minutes. After an additional 2 hours stirring at room temperature, the reaction mixture was poured onto ice water. The basic aqueous solution was washed twice with ethyl acetate (20 ml.) and acidified to pH ~ 3 with 10% aqueous hydrochloric acid. The acidic solution was extracted with ethyl acetate (3 × 20 ml.) and the combined organic extracts washed once with water (10 ml.), dried (MgSO$_4$) and evaporated to a solid residue weighing 784 mg. This solid residue was triturated with ethyl acetate and filtered. The filtrate was purified by column chromatography on silica gel (Baker "Analyzed" Reagent 60–200 mesh) using ethyl acetate as eluent. After removal of high R$_f$ impurities, 225 mg. (66%) of 9α-hydroxy-11α,15α-bis-(tetrahydropyran-2-yloxy)-19-oxa-cis-5-trans-13-prostadienoic acid was collected.

The nmr spectrum (CDCl$_3$) exhibited a multiplet (variable) at 5.84–6.38 δ (2H) for the -O$\underline{H}$ protons, a multiplet at 5.27–5.68 δ (4H) for the olefinic protons, a multiplet at 4.52–4.84 δ (2H) for the acetal protons, a singlet at 3.34 δ (3H) for the methyl ether protons and muliplets at 3.25–4.35 δ (9H) and 1.20–2.72 δ (28H) for the remaining protons.

EXAMPLE VIII

To a solution cooled to −10° under nitrogen of 190 mg. (0.356 mmole) 9α-hydroxy-11α,15α-bis-(tetrahydropyran-2-yloxy)-19-oxa-cis-5-trans-13-prostadienoic acid as prepared in Example VII, in 5 ml. reagent grade acetone was added dropwise 0.143 ml. (0.356 mmole) of Jones' reagent. After 20 minutes at −10°, 0.140 ml. 2-propanol was added and the reaction mixture was allowed to stir an additional 5 minutes at which time it was combined with 40 ml. ethyl acetate, washed with water (3 × 5 ml.), dried (MgSO$_4$) and concentrated to give 174 mg. of 9-oxo-11α,15α-bis-(tetrahydropyran-2-yloxy)-19-oxa-cis-5-trans-13-prostadienoic acid.

EXAMPLE IX

A solution of 174 mg. (0.334 mmole) 9-oxo-11α,15α-bis-tetrahydropyran-2-yloxy)-19-oxa-cis-5-trans-13-prostadienoic acid as prepared in Example VIII in 3.0 ml. of a 65:35 mixture of glacial acetic acid:water was stirred under nitrogen at 40° for 5 hours then was concentrated by rotary evaporation. The resultant crude oil was purified by column chromatography on silica gel (Mallinckrodt CC-4 100–200 mesh) using ethyl acetate as eluent. After elution of less polar impurities the semi-solid 9-oxo-11α,15α-dihydroxy-19-oxa-cis-5-trans-13-prostadienoic acid weighing 33 mg. was collected. This product is 19-oxaprostaglandin E$_2$, m.p. 58°–9° (ethyl acetate, cyclohexane).

Analysis: Calc'd for C - 64.39; H - 8.53. Found C - 64.30; H - 8.28. $[\alpha]_D^{25} = -71.2°$ (C = 1.0, methanol)

The ir spectrum (CHCl$_3$) of the product exhibited a strong adsorption at 1715 cm$^{-1}$ for the carbonyls and a medium band at 965 cm$^{-1}$ for the trans double bond. The uv spectrum in methanol with added potassium hydroxide soluion exhibited a $\lambda_{max}$ 278 mμ and an $\epsilon_{max}$ 28,000.

If the corresponding 19-oxaprostaglandin A$_2$ is desired, the above 19-oxoprostaglandin E$_2$ may be treated with formic acid, and the product then purified by column chromatography.

EXAMPLE X

A solution of 52 mg. (0.10 mmole) 9α-hydroxy-11α,15α-bis-(tetrahydropyran-2-yloxy)-19-oxa-cis-5-trans-13-prostadienoic acid as prepared in Example VII, in 3.0 ml. of a 65:35 mixture of glacial acetic acid-water was stirred under nitrogen at 40° for 5 hours then was concentrated by rotary evaporation. The resultant crude oil was purified on silica gel (Mallinckrodt CC-4 100-200 mesh) using ethyl then methanol as eluents. After elution of less polar impurities the oily 9α,11α,15α-trihydroxy-cis-5-trans-13-prostadienoic acid weighing 15 mg. was collected. This product is 19-oxoprostaglandin F$_{2\alpha}$.

EXAMPLE XI

A solution of 12.4 g. (100 mmoles) dimethyl methylphosphonate (Aldrich) in 125 ml. dry tetrahydrofuran was cooled to −78° in a dry nitrogen atmosphere. To the stirred phosphonate solution was added 40 ml. of 2.67 M N-butyllithium in hexane solution dropwise over a period of 30 minutes at such a rate that the reaction temperature never rose about −65°. After an additional 5 minutes stirring at −78°, 8.0 g. (50.0 mmole) ethyl 4-ethoxybutyrate (prepared by the method of R. Huisgen and J. Reinertshafter, Ann., 575, 197 (1952)) was added dropwise at a rate that kept the reaction temperature less than −70° (10 minutes). After 3 hours at −78° the reaction mixture was allowed to warm to ambient temperature, neutralized with 6 ml. acetic acid and rotary evaporated to a white gel. The gelatinous material was taken up in 25 ml. water, the aqueous phase extracted with 100 ml. portions of methylene chloride (3x), the combined organic extracts dried (MgSO$_4$), and concentrated (water aspirator) to a crude residue and distilled, b.p. 130°–132° (0.1 mm) to give 7.4 g. (62%) dimethyl 2-oxo-6-oxaoctylphosphonate.

The nmr spectrum (CDCl$_3$) showed a doublet centered at 3.78 δ (J = 11.5 cps, 6H) for

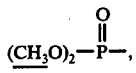

a triplet centered at 3.28 δ (2H) for CH$_3$-O-CH$_2$-, a quartet at 3.43 δ (2H) for CH$_2$-O-CH$_2$-, a doublet centered at 3.14 δ (J = 23 cps, 2H)

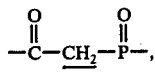

a triplet centered at 2.71 δ (2H) for

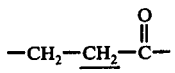

and a multiplet 1.57–2.20 δ (2H) for -CH$_2$-CH$_2$-CH$_2$ and a triplet centered at 1.15 δ (3H) for CH$_3$-CH$_2$-O-CH$_2$.

EXAMPLE XII

Dimethyl 2-oxo-6-oxaoctylphosphonate as prepared in Example XI (2.5 g., 10.7 mmole) in 175 ml. anhydrous ether was treated with 5.0 ml. (8.0 mmole) 1.6 M n-butyllithium in n-hexane in a dry nitrogen atmosphere at room temperature. After 5 minutes of stirring, an additional 350 ml. of anhydrous ether was added followed by 2.5 g. (7.2 mmole) 2-[3α-p-phenylbenzoyloxy-5α-hydroxy-2β-formylcyclopentan-1α-yl]acetic acid, γ-lactone in one portion. After 30 minutes the reaction mixture was quenched with 5.0 ml. glacial acetic acid, diluted with 200 ml. anhydrous ether, washed with 200 ml. 10% HCl (2 x), 200 ml. saturated sodium bicarbonate solution (1 x), 100 ml. water (1 x), dried (MgSO$_4$) and evaporated to yield 3.591 g. (109%) crude 2-[3α-p-phenylbenzoyloxy-5α-hydroxy-2β-(3-oxo-7-oxa-trans-1-nonen-1-yl)cyclopent-1α-yl]acetic acid, γ-lactone, as an oil.

The ir spectrum (CHCl$_3$) of the product exhibited adsorption bands at 1760 cm$^{-1}$ (strong), 1707 cm$^{-1}$ (strong), 1665 cm$^{-1}$ (medium) and 1620 cm$^{-1}$ (medium) attributable to the carbonyl groups. The nmr spectrum (CDCl$_3$) was consistent.

EXAMPLE XIII

To a solution of 3491 mg. (7.6 mmole) crude 2-[3α-p-phenylbenzoyloxy-5α-hydroxy-2β-(3-oxo-7-oxa-trans-1-nonen-1-yl)cyclopent-1α-yl]acetic acid, γ-lactone as prepared in Example XII in 30 ml. dry 1,2-dimethoxyethane in a dry nitrogen atmosphere at ambient temperature was added dropwise 7.5 ml. of a 0.5 M zinc borohydride solution. After stirring at room temperature for 1 hour, the reaction mixture was cooled to 0° and a saturated sodium bitartrate solution was added dropwise until hydrogen evolution ceased. The reaction mixture was allowed to stir for 5 minutes at which time 250 ml. dry methylene chloride was added. After drying (MgSO$_4$) and concentrating (water aspirator) the resultant semisolid was purified by column chromatography on silica gel (Baker "Analyzed" Reagent 60-200 mesh) using ether as eluent. After elution of less polar impurities, fractions containing 703 mg. 2-[3α-p-phenylbenzoyloxy-5α-hydroxy-2β-(3α-hydroxy-7-oxa-trans-1-nonen-1-yl)cyclopent-1α-yl]acetic acid, γ-lactone, a fraction containing 2-[3α-p-phenylbenzoyloxy-5α-hydroxy-2β-(3β-hydroxy-7-oxa-trans-1-nonen-1-yl)cyclopent-1α-yl]acetic acid, γ-lactone, and a fraction of the two mixed were eluted.

The ir spectrum (CHCl$_3$) of the first compound above had strong carbonyl adsorptions at 1770 and 1705 cm$^{-1}$. The nmr (CDCl$_3$) was consistent with its structure.

EXAMPLE XIV

A heterogeneous mixture of 703 mg. (1.5 mmole) of 2-[3α-p-phenylbenzo-oxy-5α-hydroxy-2β-(3α-hydroxy-7-oxa-trans-1-nonen-1-yl)cyclopent-1α-yl]acetic acid, γ-lactone as prepared in Example XIII, 7.0 ml. of absolute methanol and 207 mg. of finely powdered, anhydrous potassium carbonate was stirred at room temperature for one hour, then cooled to 0°. To the cooled solution was added 3.5 ml. (3.0 mmole) of 1.0 N aqueous hydrochloric acid. After stirring at 0° for an additional 10 minutes, 7 ml. of water was added with concomitant formation of methyl p-phenylbenzoate which was collected by filtration. The filtrate was saturated with solid sodium chloride, extracted with ethyl acetate (4 × 10 ml.), the combined organic extracts were washed with saturated sodium bicarbonate (10 ml.), dried (MgSO$_4$) and concentrated to give 350 mg. (85.5%) of viscous, oily 2-[3α,5α-dihydroxy-2β-(3α-hydroxy-7-oxa-trans-1-nonen-1-yl)cyclopent-1α-yl]acetic acid, γ-lactone.

The ir spectrum (CHCl$_3$) exhibited a strong adsorption at 1770 cm$^{-1}$ for the lactone carbonyl and medium adsorption at 965 cm$^{-1}$ for the trans-double bond.

EXAMPLE XV

To a solution of 350 mg. (1.28 mmole) 2-[3α,5α-dihydroxy-2β-(3α-hydroxy-7-oxa-trans-1-nonenyl)cyclopent-1α-yl]acetic acid, γ-lactone as prepared in Example XIV in 3.5 ml. anhydrous methylene chloride and 350 μl of 2,3-dihydropyran at 0° in a dry nitrogen atmosphere was added 3.5 mg. p-toluenesulfonic acid, monohydrate. After stirring for 15 minutes, the reaction mixture was combined with 100 ml. ether, the ether solution washed with saturated sodium bicarbonate (1 × 15 ml.) then saturated brine (1 × 15 ml.), dried (MgSO$_4$) and concentrated to yield 590 mg. (>100%) 2-[5α-hydroxy-3α-(tetrahydropyran-2-yloxy)-2β-(3α-[tetrahydropyran-2-yloxy]-7-oxa-trans-1-nonen-1-yl)cyclopent-1α-yl]acetic acid, γ-lactone.

The nmr spectrum (CDCl$_3$) exhibited a multiplet at 5.30–5.65 δ (2H) for the olefinic protons, a quartet at 3.50 δ (2H) for the ethyl ether protons, multiplets at 4.35–5.18 δ (4H), 3.22–4.24 δ (8H), and 1.18–2.92 δ (21H) and a triplet at 1.20 δ (3H).

EXAMPLE XVI

A solution of 575 mg. (1.28 mmole) crude 2-[5α-hydroxy-3α-tetrahydropyran-2-yloxy)-2β(3α-[tetrahydropyran-2-yloxy]-7-oxa-trans-1-nonen-1-yl) cyclopent-1α-yl, acetic acid, γ-lactone as prepared in Example XV in 5.75 ml. dry toluene was cooled to −78° in a dry nitrogen atmosphere. To this cooled solution was added 1.8 ml. of 20% diisobutylaluminum hydride in n-hexane dropwise at such a rate so that the internal temperature never rose above −65° (15 minutes). After an additional 1 hour of stirring at −78°, anhydrous methanol was added until gas evolution ceased and the reaction mixture was allowed to warm to room temperature. The reaction mixture was combined with 50 ml. ether, washed with 50% sodium potassium tartrate solution (4 × 10 ml.), dried (MgSO₄) and concentrated to yield 458 mg. (80%) 2-[5α-hydroxy-3α-(tetrahydropyran-2-yloxy)-2β-(3α-[tetrahydropyran-2-yloxy]-7-oxa-trans-1-nonen-1-yl)cyclopent-1-yl]acetaldehyde, γ-hemiacetal.

EXAMPLE XVII

To a solution of 1330 mg. (3.0 mmole) (4-carbohydroxy-n-butyl)triphenylphosphonium bromide in a dry nitrogen atmosphere in 6 ml. dry dimethyl sulfoxide was added 3.4 ml. (6.8 mmole) of a 2.0 M solution of sodium methylsulfinylmethide in dimethyl sulfoxide. To this red ylide solution was added dropwise a solution of 454 mg. (1.0 mmole) crude 2-[5α-hydroxy-3α-(tetrahydropyran-2-yloxy)-2β-(3α-[tetrahydropyran-2-yloxy]-7-oxa-trans1-nonen-1-yl)cyclopent-1α-yl]acetaldehyde, γ-hemiacetal as prepared in Example XVI in 3.0 ml. dry dimethyl sulfoxide over a period of 20 minutes. After 2 hours stirring at room temperature, the reaction mixture was poured onto ice water. The basic aqueous solution was washed twice with ethyl acetate (30 ml.) and acidified to pH ∼ 3 with 10% aqueous hydrochloric acid. The acidic solution was extracted with ethyl acetate (4 × 25 ml.) and the combined organic extracts washed once with water (25 ml.), dried (MgSO₄) and evaporated to a solid residue weighing 900 mg. This solid residue was triturated with ethyl acetate and filtered. The filtrate was purified by column chromatography on silica gel (Baker "Analyzed" Reagent 60-200 mesh) using ethyl acetate as eluent. After removal of high R_f impurities, 290 mg. (54%) of 9α-hydroxy-11α,15α-bis-(tetrahydropyran-2-yloxy)-19-oxa-cis-5-trans-13-w-homo-prostadienoic acid was collected.

The nmr spectrum (CDCl₃) exhibited a multiplet (variable) at 6.2–6.6 δ (2H) for the -O$\underline{H}$ protons, a multiplet at 5.3–5.7 δ (4H) for the olefinic protons, a multiplet at 4.6–4.9 δ (2H) for the acetal protons, a quartet at 3.5 δ (2H) for the ethyl ether protons and multiplets at 3.3–4.4 δ (9H) and 1.0–2.6 δ (31H) for the remaining protons.

EXAMPLE XVIII

To a solution cooled to −10° under nitrogen of 290 mg. (0.540 mmole) 9α-hydroxy-11α,15α-bis-(tetrahydropyran-2-yloxy)-19-oxa-cis-5-trans-13-w-homo-prostadienoic acid, as prepared in Example XVII, in 5.4 ml. reagent grade acetone was added dropwise 0.226 ml. (0.600 mmole) of 2.67 M Jones' reagent. After 5 minutes at −10°, 0.230 ml. 2-propanol was added and the reaction mixture was allowed to stir an additional 5 minutes at which time it was combined with 30 ml. ethyl acetate, washed with water (3 × 5 ml.), dried (MgSO₄), concentrated, and chromatographed (Baker 60-200 mesh silica gel, CH₂Cl₂ eluent) to give 180 mg. of 9-oxo-11α,15α-bis-(tetahydropyran-2-yloxy)-19-oxa-cis-5-trans-13-w-homo-prostadienoic acid.

EXAMPLE XIX

A solution of 129 mg. (0.240 mmole) 9-oxo-11α,15α-bis-tetrahydropyran2-yloxy)-19-oxa-cis-5-trans-13-w-homo-prostadienoic acid, as prepared in Example XVIII, in 3.0 ml. of a 65:35 mixture of glacial acetic acid:water was stirred under nitrogen at 40° for 2.5 hours then was concentrated by rotary evaporation. The resultant crude oil was purified by column chromatography on silica gel (Mallinckrodt CC-4 100-200 mesh) using ethyl acetate as eluent. After elution of less polar impurities 9-oxo-11α,15α-dihydroxy-19-oxa-cis-5-trans-13-w-homo-prostadienoic acid (11) weighing 40 mg. was collected (m.p. 56°-7°). This product is 19-oxa-w-homoprostaglandin E₂.

The uv spectrum in methanol with added potassium hydroxide solution exhibited a λ$_{max}$ 278 mμ and an ε$_{max}$ 25,700.

If 19-oxa-w-homoprostaglandin A₂ is desired, the procedure outlined in Example IX may be followed.

If 19-oxa-w-homoprostaglandin F$_{2α}$ is desired, the procedure outlined in Example X may be followed, using the product of Example XVIII as a starting material.

EXAMPLE XX

A solution of 12.4 g. (100 mmoles) dimethyl methylphosphonate (Aldrich) in 125 ml. dry tetrahydrofuran was cooled to −78° in a dry nitrogen atmosphere. To the stirred phosphonate solution was added 40 ml. of 2.67 M n-butyllithium in hexane solution (Alfa Inorganics, Inc.) dropwise over a period of 30 minutes at such a rate that the reaction temperature never rose about −65°. After an additional 5 minutes stirring at −78°, 7.6 g. (50.0 mmole) ethyl 3-ethoxypropionate was added dropwise at a rate that kept the reaction temperature less than −70° (10 minutes). After 3 hours at −78° the reaction mixture was allowed to warm at ambient temperature, neutralized with 6 ml. acetic acid and rotary evaporated to a white gel. The gelatinous material was taken up in 25 ml. water, the aqueous phase extracted with 100 ml. portions of ether (3x), the combined organic extracts dried (MgSO₄), and concentrated (water aspirator) to a crude residue and distilled, b.p. 107°-114° (0.1 mm) to give 5.6 g. (50%) dimethyl 2-oxo-5-oxaheptylphosphonate (2).

The nmr spectrum (CDCl₃) showed a doublet centered at 3.79 δ (J = 11.5 cps, 6H) for

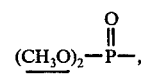

a triplet centered at 3.28 δ (2H), for CH₃-O-C$\underline{H_2}$-CH₂-, a quartet at 3.43 δ (2H) for C$\underline{H_2}$-O-CH₂-, a doublet centered at 3.14 δ (J = 23 cps, $\overline{2H}$)

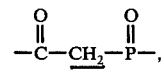

a triplet centered at 2.87 δ (2H) for

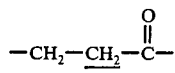

and a triplet centered at 1.19 δ (3H) for CH₃-CH₂-O-CH₂.

EXAMPLE XXI

Dimethyl 2-oxo-5-oxaheptylphosphonate, as prepared in Example XX, (3.8 g., 17.1 mmole) in 200 ml. anhydrous ether was treated with 4.8 ml. (12 mmole) 2.5 M n-butyllithium in n-hexane in a dry nitrogen atmosphere at room temperature. After 5 minutes of stirring, an additional 400 ml. of anhydrous ether was added followed by 4 g. (11.4 mmole) 2-[3α-p-phenylbenzoyloxy-5α-hydroxy-2β-formylcyclopentan-1α-yl]acetic acid, γ-lactone in one portion. After 35 minutes the reaction mixture was quenched with 5.0 ml. glacial acetic acid, diluted with 200 ml. anhydrous ether, washed with 200 ml. 10% HCl (2 x), 200 ml. saturated sodium bicarbonate solution (1 x), 100 ml. water (1 x), dried (MgSO₄) and evaporated to yield 4.057 (80%) crude 2-[3α-p-phenylbenzoyloxy-5α-hydroxy-2β-(3-oxo-6-oxa-trans-1-octen-1-yl)cyclopent-1α-yl]acetic acid, γ-lactone as an oil.

The ir spectrum (CHCl₃) of the product exhibited adsorption bands at 1770 cm⁻¹ (strong), 1707 cm⁻¹ (strong), 1670 cm⁻¹ (medium) and 1620 cm⁻¹ (medium) attributable to the carbonyl groups. The nmr spectrum (CDCl₃) was consistent.

EXAMPLE XXII

To a solution of 4100 mg. (9.2 mmole) crude 2 -[3α-p-phenylbenzoyloxy-5α-hydroxy-2β-(3-oxo-6-oxa-trans-1-octen-1-yl)cyclopent-1α-yl]acetic acid, γ-lactone in 30 ml. dry 1,2-dimethoxyethane in a dry nitrogen atmosphere at 0° C. was added dropwise 4.5 ml. of a 1.0 M zinc borohydride solution. After stirring at 0° C. for 1 hour, a saturated sodium bitartrate solution was added dropwise until hydrogen evolution ceased. The reaction mixture was allowed to stir for 5 minutes at which time 200 ml. dry methylene chloride was added. After drying (MgSO₄) and concentrating (water aspirator) the resultant semisolid was purified by column chromatography on silica gel (Baker "Analyzed" Reagent 60-200 mesh) using ether/ethyl acetate (5:1) as eluent. After elution of less polar impurities, fractions containing 778 mg. 2-[3α-p-phenylbenzoyloxy-5α-hydroxy-2β-(3α-hydroxy-6-oxa-trans-1-octen-1-yl)cyclopent-1α-yl]acetic acid, γ-lactone (5), 2-[3α-p-phenylbenzoyloxy-5α-hydroxy-2β-(3β-hydroxy-6-oxa-trans-1-octen-1-yl)cyclopent-1α-yl]acetic acid, γ-lactone, and 355 mg. of the 2 mixed were eluted.

The ir spectrum (CHCl₃) of the first of the above fractions had strong carbonyl adsorptions at 1775 and 1715 cm⁻¹. The nmr (CDCl₃) was consistent with its structure.

EXAMPLE XXIII

A heterogeneous mixture of 1006 mg. (2.24 mmole) of 2-[3α-p-phenylbenzoyloxy-5α-hydroxy-2β-(3α-hydroxy-6-oxa-trans-1-octen-1-yl)cyclopent-1α-yl]acetic acid, γ-lactone, as prepared in Example XXII, 10.0 ml. of absolute methanol and 310 mg. of finely powdered, anhydrous potassium carbonate was stirred at room temperature for one hour, then cooled to 0°. To the cooled solution was added 10 ml. (10 mmole) of 1.0 N aqueous hydrochloric acid. After stirring at 0° for an additional 10 minutes, 10 ml. of water was added with concomitant formation of methyl p-phenylbenzoate which was collected by filtration. The filtrate was saturated with solid sodium chloride, extracted with ethyl acetate (2 × 100 ml.), the combined organic extracts were washed with saturated sodium bicarbonate (2 × 25 ml.), dried (MgSO₄) and concentrated to give 570 mg. (94%) of viscous, oily 2-[3α,5α-dihydroxy-2β-(3α-hydroxy-6-oxa-trans-1-octen-1-yl)cyclopent-1α-yl]acetic acid, γ-lactone.

The ir spectrum (CHCl₃) exhibited a strong adsorption at 1770 cm⁻¹ for the lactone carbonyl and medium adsorption at 965 cm⁻¹ for the trans-double bond.

EXAMPLE XXIV

To a solution of 570 mg. (2.11 mmole) 2-[3α,6α-dihydroxy-2β-(3α-hydroxy-6-oxa-trans-1-octen)cyclopent-1α-yl]acetic acid, γ-lactone, prepared as in Example XXIII, in 5.7 ml. anhydrous methylene chloride and 570 μl of 2,3-dihydropyran at 0° in a dry nitrogen atmosphere was added 5.7 mg. p-toluenesulfonic acid, monohydrate. After stirring for 15 minutes, the reaction mixture was combined with 200 ml. ether, the ether solution washed with saturated sodium bicarbonate (1 × 25 ml.) then saturated brine (1 × 25 ml.), dried (MgSO₄) and concentrated to yield 925 mg. (100%) 2-[5α-hydroxy-3α-(tetrahydropyran-2-yloxy)2β-(3α-[tetrahydropyran-2-yloxy]-6-oxa-trans-1-octen-1-yl)cyclopent-1α-yl]acetic acid, γ-lactone.

The nmr spectrum (CDCl₃) exhibited a multiplet at 5.30–5.70 δ (2H) for the olefinic protons, a quartet at 3.40 δ (2H) for the ethyl ether protons, multiplets at 4.35–5.18 δ (4H), 3.18–4.32 δ (8H), and 1.18–2.92 δ (25H) and a triplet at 1.10 δ (3H).

EXAMPLE XXV

A solution of 880 mg. (2.01 mmole) crude 2-[5α-hydroxy-3α-tetrahydropyran-2-yloxy)-2α-(3α-[tetrahydropyran-2-yloxy]-6-oxa-trans-1-octen-1-yl]cyclopent-1α-yl, acetic acid, γ-lactone, prepared as in Example XXIV, in 8.8 ml. dry toluene was cooled to −78° in a dry nitrogen atmosphere. To this cooled solution was added 3 ml. of 20% diisobutylaluminum hydride in n-hexane dropwise at such a rate so that the internal temperature never rose about −65° (15 minutes). After an additional 30 minutes of stirring at −78°, anhydrous methanol was added until gas evolution ceased and the reaction mixture was allowed to warm to room temperature. The reaction mixture was combined with 100 ml. ether, washed with 50% sodium potassium tartrate solution (4 × 10 ml.), dried (MgSO₄) and concentrated to yield 654 mg. 2-[5α-hydroxy-3α-(tetrahydropyran-2-yloxy)-2β-(3α-[tetrahydropyran-2-yloxy]-6-oxa-trans-1-octen-1-yl]-yl-)cyclopent-1-yl]acetaldehyde, γ-hemiacetal.

EXAMPLE XXVI

To a solution of 2600 mg. (6.0 mmole) (4-carbohydroxy-n-butyl)triphenylphosphonium bromide in a dry nitrogen atmosphere in 6 ml. dry dimethyl sulfoxide was added 6.0 ml. (12.0 mmole) of a 2.0 M solution of sodium methylsulfinylmethide in dimethyl sulfoxide. To this red ylide solution was added dropwise a solution of 660 mg. (1.5 mmole) crude 2-[5α-hydroxy-3α-(tetrahydropyran-2-yloxy)-2β-(3α-]tetrahydropyran-2-yloxy]-6-oxa-trans-1-octen-1-yl)cyclopent-1α-yl]acetaldehyde, γ-hemiacetal, prepared as in Example XX in 5.0 ml. dry dimethyl sulfoxide over a period of 20 minutes. After an additional 2 hours stirring at room temperature, the reaction mixture was poured onto ice water. The basic aqueous solution was washed twice with ethyl acetate (100 ml.) and acidified to pH ~ 3 with 10% aqueous hydrochloric acid. The acidic solution was extracted with ethyl acetate (3 × 100 ml.) and the combined organic extracts washed once with water (25 ml.), dried (MgSO$_4$) and evaporated to a solid residue. This solid residue was triturated with ethyl acetate and filtered. The filtrate was purified by column chromatography on silica gel (Baker "Analyzed" Reagent 60-200 mesh) using ethyl acetate as eluent. After removal of high R$_f$ impurities, 550 mg. (70% of 9α-hydroxy-11α,15α-bis-(tetrahyropyran-2-yloxy)-18-oxa-cis-5-trans-13-prostadienoic acid was collected.

The nmr spectrum (CDCl$_3$) exhibited a multiplet (variable) at 6.2–6.6 δ (2H) for the -OH protons, a multiplet at 5.3–5.7 δ (4H) for the olefinic protons, a multiplet at 4.6–4.9 δ (2H) for the acetal protons, a quartet at 3.5 δ (2H) for the ethyl ether protons and multiplets at 3.3–4.4 δ (9H) and 1.0–2.6 δ (31H) for the remaining protons.

EXAMPLE XXVII

To a solution cooled to −10° under nitrogen of 400 mg. (0.765 mmole) 9α-hydroxy-11α,15α-bis-(tetrahydropyran-2-yloxy)-18-oxa-cis-5-trans-13-prostadienoic acid, prepared as in Example XXVI, in 8 ml. reagent grade acetone was added dropwise 0.338 ml. (0.900 mmole) of 2.67 M Jones' reagent. After 5 minutes at −10°, 0.350 ml. 2-propanol was added and the reaction mixture was allowed to stir an additional 5 minutes at which time it was combined with 60 ml. ethyl acetate, washed with water (3 × 5 ml.), dried (MgSO$_4$), and concentrated to give 280 mg. of 9-oxo-11α,15α-bis-(tetrahydropyran-2-yloxy)-18-oxa-cis-5-trans-13-prostadienoic acid.

EXAMPLE XXVIII

A solution of 280 mg. (0.240 mmole) 9-oxo-11α,15α-bis-tetrahydropyran-2-yloxy)-18-oxa-cis-5-trans-13-prostadienoic acid, prepared as in Example XXVII in 4.0 ml. of a 65:35 mixture of glacial acetic acid:water was stirred under nitrogen at 40° for 2.5 hours then was concentrated by rotary evaporation. The resultant crude oil was purified by column chromatography on silica gel (Mallinckrodt CC-4 100–200 mesh) using ethyl acetate as eluent. After elution of less polar impurities the oily 9-oxo-11α,15α-dihydroxy-18-oxa-cis-5-trans-13-prostadienoic acid weighing 66 mg. was collected. This product is 18-oxaprostaglandin E$_2$.

The uv spectrum in methanol with added potassium hydroxide solution exhibited a λ$_{max}$ 278 mμ and an ε$_{max}$ 23,800 to 25,600.

If the corresponding 18-oxaprostaglandin A$_2$ is desired, the procedures of Example IX may be carried out.

EXAMPLE XXIX

A solution of 75 mg. (0.10 mmole) 9α-hydroxy-11α,-15α-bis-(tetrahydropyran-2-yloxy)-18-oxa-cis-5-trans-13-prostdienoic acid, prepared as in Example XXVII, in 3.0 ml. of a 65:35 mixture of glacial acetic acid:water was stirred under nitrogen at 40° for 5 hours then was concentrated by rotary evaporation. The resultant crude oil was purified on silica gel (Mallinckrodt CC-4 100–200 mesh) using ethyl then methanol as eluents. After elution of less polar impurities the oily 9α,11α,- 15α-trihydroxy-18-oxa-cis-5-trans-13-prostadienoic acid weighing 20 mg. was collected. This product is 18-oxaprostaglandin F$_{2α}$.

EXAMPLE XXX

To a solution of 76 mg. of 19-oxa-PGF$_{2α}$ in 1.0 ml. of pyridine is added 120 mg. (1.0 mmole) of pivaloyl chloride. The solution is stirred for 5 hours at 45° under nitrogen then is cooled to room temperature. To the solution is then added 36 mg. (2.0 mmoles) of water. The solution is then stirred at room temperature for 2.0 hours, then is diluted with ethyl acetate. The diluted solution is washed with 0.1 N hydrochloric acid (3x), with water (1x), and with saturated brine (1x), is dried (anhydrous magnesium sulfate), and is concentrated. Purification of the crude residue by silica gel chromatography provides the desired 9α,11α,15α-tris-pivaloyloxy 19-oxa PGF$_{2α}$.

EXAMPLE XXXI

To a solution of 37 mg. of 19-oxa-PGA$_2$ in 0.5 ml. of dry tetrahydrofuran is added 29 mg. (0.33 mmole) of formic acetic anhydride and 35 mg. (0.33 mmoles) of 2,6-lutidine. The solution is stirred for 4 hours under nitrogen at room temperature then 36 mg. (2.0 mmoles) of water is added. The mixture is stirred at room temperature for an additional 1.0 hour then is diluted with ethyl actuated. The diluted solution is washed with 0.1 N hydrochloric acid (1x), with water (1x), and with saturated brine (1x), is dried (anhydrous magnesium sulfate), and is concentrated. Purification of the crude residue by silica gel chromatography affords the 15α-formyl-19-oxa PGA$_2$.

EXAMPLE XXXII

To a solution, cooled in ice under nitrogen, of 75 mg. of 19-oxa-ω-homo PGE$_2$ in 1.5 ml. of methylene chloride is added 350 μl. of pivaloyl chloride followed by 450μl. of triethylamine. After being stirred at room temperature for 5 hours the mixture is poured onto a mixture of ethyl acetate/ice. The aqueous layer is extracted with ethyl acetate; the combined organic extracts are washed with 10% hydrochloric acid, with saturated bicarbonate, with water, is dried (anhydrous magnesium sulfate), and is concentrated. Purification of the crude product by chromatography provides the desired 11α,15α-bis-pivaloyloxy 19-oxa-ω-homo-PGE$_2$.

EXAMPLE XXXIII

To a solution, cooled in ice under nitrogen, of 125 mg. of 18-oxa-PGE$_2$ in 2.5 ml. of methylene chloride is added 0.50 ml. of benzoyl chloride followed by 0.625 ml. of triethylamine. After being stirred at room temperature for 5 hours, the mixture is poured onto a mixture of ethyl acetate:ice water. The aqueous layer is further extracted with ethyl acetate; the combined organic extracts are washed with 10% hydrochloric acid and with water, is dried (anhydrous magnesium sulfate), and is concentrated. Purification of the crude products by chromatography provides the desired 11α,15α-dibenzoyloxy-18-oxA PGE$_2$ and 15α-benzoyloxy-18-oxa-PGA$_2$.

EXAMPLE XXXIV

To a solution, cooled in ice, of 35 mg. of 19-oxa-PGE$_2$ prepared in Example IX in 7 ml. of absolute methanol is added an ice-chilled solution of 105 mg. of sodium borohydride in 12 ml. of absolute methanol. The solution is stirred under nitrogen for 20 minutes at 0°–5° then for 1.0 hour at room temperature. The reaction mixture is then cooled in ice, 2 ml. of water is added, and the resultant solution is concentrated. The concentrated mixture is overlaid with ethyl acetate, acidified with 10% hydrochloric acid, and the acidified aqueous layer is extracted with ethyl acetate (4 × 5 ml.). The combined extracts are washed with water and saturated brine, dried (anhydrous magnesium sulfate), and concentrated. The crude residue is purified by column chromatography (Mallinckrodt CC-7) using mixtures of methanol in methylene chloride as eluents to afford 19-oxa PGF$_{2\alpha}$ and 19-oxa PGF$_{2\beta}$.

What is claimed is:

1. A compound of the structure

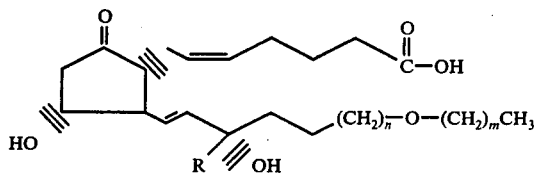

wherein R is hydrogen or alkyl having 1 to 3 carbon atoms, n is an integer of from 0 to 1 and m is an integer of from 0 to 4.

2. 9-oxo-11α,15α-dihydroxy-19-oxa-cis-5-trans-13-prostadienoic acid.

3. 9-oxo-11α,15α-dihydroxy-19-oxa-cis-5-trans-13-ω-homoprostadienoic acid.

4. 9-oxo-11α,15α-dihydroxy-18-oxa-cis-5-trans-13-prostadienoic acid.

* * * * *

UNITED STATES PATENT AND TRADEMARK OFFICE
CERTIFICATE OF CORRECTION

PATENT NO. : 4,094,899
DATED : June 13, 1978
INVENTOR(S) : Hans-Jurgen E. Hess

It is certified that error appears in the above-identified patent and that said Letters Patent are hereby corrected as shown below:

Front page, data element identifier "[75]", after "Hess," "Old Lime, China/Taiwan" should read -- Old Lyme, Conn. --.

Signed and Sealed this

Fifth Day of December 1978

[SEAL]

Attest:

RUTH C. MASON
Attesting Officer

DONALD W. BANNER
Commissioner of Patents and Trademarks